United States Patent [19]

Upadek et al.

[11] 4,360,468
[45] Nov. 23, 1982

[54] PREPARATION OF 13-OXABICYCLO[10.3.0]PENTADECANE

[75] Inventors: Horst Upadek, Erkrath; Klaus Bruns, Krefeld-Traar, both of Fed. Rep. of Germany

[73] Assignee: Henkel Kommanditgesellschaft auf Aktien, Düsseldorf-Holthausen, Fed. Rep. of Germany

[21] Appl. No.: 306,771

[22] Filed: Sep. 29, 1981

[30] Foreign Application Priority Data

Oct. 31, 1980 [DE] Fed. Rep. of Germany ....... 3040994

[51] Int. Cl.$^3$ ............................................ C07D 307/93
[52] U.S. Cl. .................................................. 549/462
[58] Field of Search .............................. 260/346.22 R

[56] References Cited

FOREIGN PATENT DOCUMENTS 1093568 1/1981 Canada .
2810107 9/1979 Fed. Rep. of Germany .
1466245 1/1967 France .

Primary Examiner—Henry R. Jiles
Assistant Examiner—Bernard Dentz
Attorney, Agent, or Firm—Hammond & Littell, Weissenberger and Muserlian

[57] ABSTRACT

This invention relates to the preparation of 13-oxabicyclo[10.3.0]pentadecane. More specifically, this invention relates to a process for preparing 13-oxabicyclo[10.3.0]pentadecane which comprises the steps of:
(a) reacting cyclododecanone with elemental bromine in an organic solvent to form α-bromocyclododecanone;
(b) reacting α-bromocyclododecanone with malonic acid dialkyl ester and alkali metal alcoholate to form the ketodiester 2-(2-oxocyclododec-1-yl)-malonic acid dialkyl ester;
(c) hydrolyzing and decarboxylating the ketodiester from step (b) to from the corresponding 2-oxocyclododec-1-yl-acetic acid in an aqueous alkaline solution;
(d) purifying the product of step (c) by extraction with an organic solvent and obtaining 2-oxocyclododec-1-yl-acetic acid;
(e) reacting the product of step (d) with a lower alcohol to form a corresponding ester;
(f) reducing the product of step (e) with a complex metallic hydride to form 2-(2-hydroxyethyl)-cyclododecanol; and
(g) heating the product of step (f) in the presence of an acid catalyst to form 13-oxabicyclo[10.3.0]pentadecane.

8 Claims, No Drawings

PREPARATION OF 13-OXABICYCLO[10.3.0]PENTADECANE

FIELD OF THE INVENTION

This invention relates to the preparation of 13-oxabicyclo[10.3.0]pentadecane. More specifically, this invention relates to an improved process for the preparation of 13-oxabicyclo[10.3.0]pentadecane in the absence of bromoacetic acid ester.

BACKGROUND OF THE INVENTION

The compound 13-oxabicyclo[10.3.0]pentadecane is a valuable fragrance with a warm ambergris note and exceptionally good staying power. The preparation of this substance is described in the Canadian Pat. No. 1,093,568, incorporated herein by reference. The synthesis described can be shown by the following scheme:

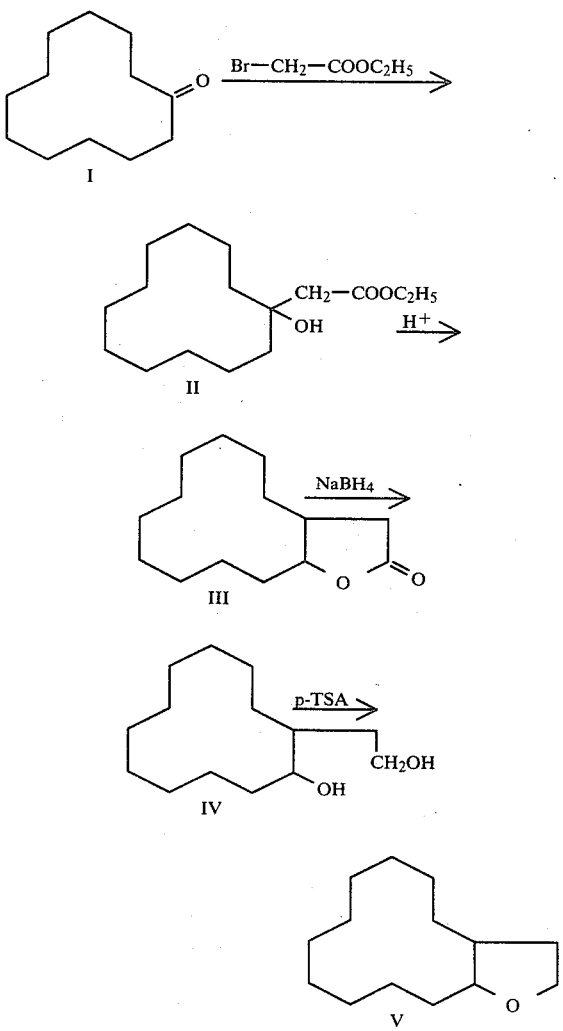

According to this synthesis, cyclododecanone (I) is converted with bromoacetic acid ester by means of the Reformatsky reaction to the corresponding hydroxy ester (II), which rearranges itself readily into a lactone (III) with heating in a highly acid medium. This lactone is reduced with sodium borohydride in isopropanol to form the diol (IV), from which the 13-oxabicyclo[10.3.0]pentadecane (V) is obtained in the form of a mixture of two stereoisomers in a molar ratio of approximately 2:1 by intramolecular removal of water in toluene, in the presence of p-toluenesulfonic acid (p-TSA).

The use of the highly toxic, volatile bromoacetic acid ester, which irritates the mucous membranes, requires special safeguards obtainable only with a correspondingly expensive technology. Consequently there has been a need for a synthesis that does not utilize bromoacetic acid ester for the introduction of a carboxymethyl group.

OBJECTS OF THE INVENTION

It is an object of the invention to provide a process for the preparation of 13-oxabicyclo[10.3.0]pentadecane.

It is also an object of the invention to provide an improved process for the preparation of 13-oxabicyclo[10.3.0]pentadecane in the absence of bromoacetic acid ester.

It is a further object of the invention to provide a process for the preparation of 13-oxabicyclo[10.3.0]pentadecane which comprises the steps of:

(a) reacting cyclododecanone with elemental bromine in an organic solvent to form α-bromocyclododecanone;

(b) reacting α-bromocyclododecanone with malonic acid dialkyl ester and alkali metal alcoholate to form the ketodiester 2-(2-oxocyclododec-1-yl)-malonic acid dialkyl ester;

(c) hydrolyzing and decarboxylating the ketodiester from step (b) to form the corresponding 2-oxocyclododec-1-yl-acetic acid in an aqueous alkaline solution;

(d) purifying the product of step (c) by extraction with an organic solvent and obtaining 2-oxocyclododec-1-yl-acetic acid;

(e) reacting the product of step (d) with a lower alcohol to form a corresponding ester;

(f) reducing the product of step (e) with a complex metallic hydride to form 2-(2-hydroxyethyl)-cyclododecanol; and (g) heating the product of step (f) in the presence of an acid catalyst to form 13-oxabicyclo[10.3.0]pentadecane.

These and other objects of the invention will become more apparent in the discussion below.

DETAILED DESCRIPTION OF THE INVENTION

The problem of preparing 13-oxabicyclo[10.3.0]pentadecane in the absence of bromoacetic acid ester has been solved according to the invention with a new synthesis consisting of individual reaction steps that each represent a known method of preparative organic chemistry. This synthesis, which starts with cyclododecanone, represents a new and technically valuable process for the synthesis of the fragrance component 13-oxabicyclo[10.3.0]pentadecane, which can be used for many purposes. In addition, reaction conditions have been found for the individual reaction steps in the process of preparation according to the invention that largely inhibit the formation of undesirable by-products and facilitate obtaining the final product in the purity required for a fragrance with simple, technically advantageous purification operations. According to the invention, 13-oxabicyclo[10.3.0]pentadecane is prepared by means of a process which comprises the steps of:

(a) reacting cyclododecanone with elemental bromine in an organic solvent to form α-bromocyclododecanone;

(b) reacting α-bromocyclododecanone with malonic acid dialkyl ester and alkali metal alcoholate to form the ketodiester 2-(2-oxocyclododec-1-yl)-malonic acid dialkyl ester;

(c) hydrolyzing and decarboxylating the ketodiester from step (b) to form the corresponding 2-oxocyclododec-1-yl-acetic acid in an aqueous alkaline solution;

(d) purifying the product of step (c) by extraction with an organic solvent and obtaining 2-oxocyclododec-1-yl-acetic acid;

(e) reacting the product of step (d) with a lower alcohol to form a corresponding ester;

(f) reducing the product of step (e) with a complex metallic hydride to form 2-(2-hydroxyethyl)-cyclododecanol; and (g) reacting the product of step (f) in the presence of an acid catalyst to form 13-oxabicyclo[10.3.0]pentadecane.

Applicant's invention can be represented by the following reaction scheme:

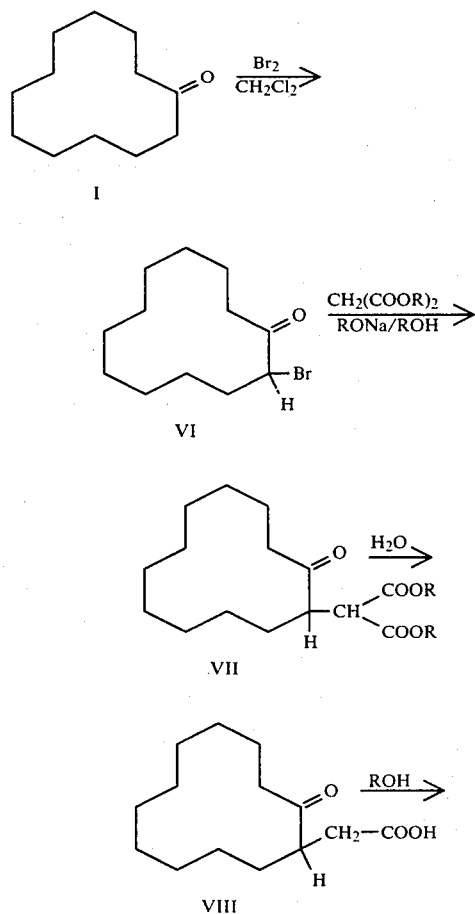

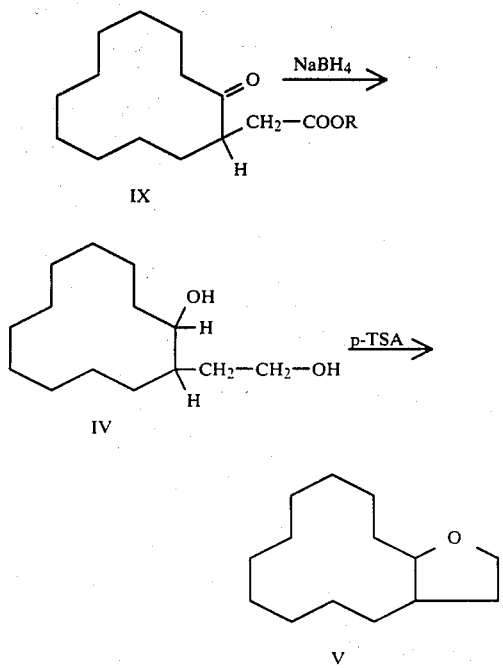

According to the synthesis, cyclododecanone (I) is used as starting compound. The compound α-bromocyclododecanone (VI) is prepared by bromination with elemental bromine in a suitable organic solvent, which compound is then reacted with sodium malonic acid dialkyl ester (that is, a mixture of malonic acid dialkyl ester, sodium alkylate, and alkanol) under strictly controlled reaction conditions to form the 2-(2-oxocyclododec-1-yl)-malonic acid dialkyl ester (VII). Saponification and decarboxylation yields the 2-oxocyclododec-1-yl-acetic acid (VIII), which, in the form of the aqueous solution of its sodium salt in alkaline solution, is readily separated from neutral by-products by washing with an organic solvent. After esterification with a lower alcohol, such as methanol or ethanol, the reduction of the ketoester (IX) with a complex metallic hydride to the 2-(2-hydroxyethyl)-cyclododecanol (IV) is carried out. The last step of the synthesis is identical with that in the process described in Canadian Pat. No. 1,093,568 and consists of the removal of water in toluene in the presence of an acid catalyst, with the formation of the cyclic ether (V).

Numerous solvents are suggested in the literature for the bromination of cyclododecanone, of which the most used, chloroform and tetrachloromethane, are suspected of being human carcinogens and are thus not suitable for technical syntheses. It has been found that the bromination may also be performed, for example, in a solvent mixture of glacial acetic acid and acetic anhydride at a molar ratio of about 7:2. The use of boiling methylene chloride as solvent has proven especially suitable for a high yield of up to 90% of theory.

Crude α-bromocyclododecanone can be used without further purification for the malonic ester synthesis. The technically easy to handle sodium methylate, used as 30% solution in methanol, is particularly suitable as base for the preparation of the salt of malonic ester. Therefore, dimethylmalonate is also advantageously used for this reaction. To prevent the formation of undesirable by-products, for example, by Favorsky rearrangement of the α-bromocyclododecanone, quick reaction of the α-bromocyclododecanone with the sodium dimethyl malonate with cooling and maintaining a temperature of from about 10° to 40° C., preferably from about 20° to 30° C., has been found to be advantageous. After removal of the solvent and neutralization with cold aqueous hydrochloric acid, the reaction product is extracted with methylisobutyl ketone.

The hydrolysis and decarboxylation of the ketodiester (VII) can be performed as usual by saponification with dilute sodium hydroxide solution and subsequent heating in a weakly acid, aqueous medium. However, it has been found that a considerably purer reaction product is obtained when the hydrolysis and decarboxylation are carried out in the presence of water at from about 200° to 250° C. in the pressure vessel and thereafter any unsaponified remaining ketomonoester is hydrolyzed with dilute aqueous sodium hydroxide solution in a second saponification step.

The aqueous solution of the sodium salt of the crude ketocarboxylic acid (VIII) obtained by this method can be separated easily from neutral by-products by washing with an organic solvent, preferably with methylisobutyl ketone. This purification operation is of crucial importance for the fragrance quality of the final product. After acidification, the 2-oxocyclodec-1-yl-acetic acid (VIII) separates in crystals with a yield of approximately 90%. (This compound was previously obtained in considerably smaller yields by a different method that is described in French Pat. No. 1,466,205.)

The keto acid (VIII) can be converted quantitatively into the methyl ester (IX) by esterification with methanol in the presence of an acid catalyst by known methods.

The reduction of the ketoester (IX) generally can be accomplished with complex metallic hydrides; however, it has been found that sodium borohydride should be given preference over other reducing agents for its ease of handling and the selective hydrogenation to form 2-(2-hydroxyethyl)-cyclododecanol (IV). According to the invention, an amount of from approximately 2 to 3 mols of sodium borohydride per mol of ketoester is needed for the complete reduction of the ketoester. After a conventional work-up, the diol (IV) is obtained with a yield of approximately 95% and is, without further purification, subjected to the removal of water known from Canadian Pat. No. 1,093,568 in an organic solvent, for example, toluene, in the presence of an acid catalyst, for example, p-toluenesulfonic acid, to form 13-oxabicyclo[10.3.0]pentadecane (V).

The following example is intended to illustrate the invention and should not be construed as limiting the invention thereto.

EXAMPLE

Preparation of 13-Oxabicyclo[10.3.0]pentadecane

1. α-Bromocyclododecanone (VI)

An amount of 183.8 gm (1.15 mol) of bromine was added dropwise with refluxing under a nitrogen atmosphere to a well agitated solution comprising 182.3 gm (1 mol) of cyclododecanone in 275 ml of methylene chloride over a period of six hours. Agitation was continued for 15 minutes and approximately one-half of the solvent was distilled off. The solution obtained by this method contained approximately 235 gm of α-bromocyclododecanone (90% yield) and was further reacted directly.

2-(2-Oxocyclododec-1-yl)-malonic acid dimethyl ester (VII)

To form a sodium malonic ester, 191 gm (1.44 mol) of malonic acid dimethyl ester was added dropwise with agitation under a nitrogen atmosphere to 252 gm of a 30% sodium methylate/methanol solution (1.40 mol of sodium methylate) in such a manner that the temperature did not rise above 50° C., and the mixture was agitated for 1 hour at 40° C. Subsequently the solution of crude α-bromocyclododecanone (approximately 0.9 mol) obtained in step 1 was added to the sodium malonic ester over a period of 30 minutes, at room temperature. The exothermic reaction was kept at about 20° to 30° C. with cooling. After the addition was complete, most of the methylene chloride and methanol was removed. The residue was neutralized with dilute, cold hydrochloric acid and extracted twice with methylisobutyl ketone. After the organic phases were combined and the volatile components were removed under reduced pressure, the crude ketodiester (VII) (approximately 250 gm; 90% yield) was obtained and used for the saponification below without any further purification.

3. 2-Oxocyclododec-1-yl-acetic acid (VIII)

After the addition of approximately 250 ml of water, the crude ketodiester (approximately 250 gm; 0.8 mol) from step 2 was hydrolyzed and simultaneously decarboxylated in an autoclave at 220° C. over a period of 6 hours. The mixture was made alkaline with approximately 1 liter of 5% sodium hydroxide solution and was agitated for 2 hours at about 40° to 50° C. to complete the saponification. The aqueous phase was washed once with 1 liter of methylisobutyl ketone to remove neutral by-products and was then acidified with concentrated sulfuric acid. The ketomono acid separated as supernatant and was dried at approximately 80° C. by applying vacuum, after the aqueous phase was decanted. An amount of approximately 175 gm of crystalline acid (90% yield) with a melting point of 124° C. was obtained.

4. 2-Oxocyclododec-1-yl-acetic acid methyl ester (IX)

One hundred seventy-five grams (0.73 mol) of the ketomono acid from step 3 and 440 ml of methanol were refluxed with agitation for 3 hours with the addition of 7.3 gm of concentrated sulfuric acid. The cooled solution was neutralized with 50% sodium hydroxide solution and then methanol and water were completely removed. The residue contained, in addition to small amounts of salt (approximately 10 gm of $Na_2SO_4$), approximately 180 gm of ketomonoester (IX) (97% yield), which was further reacted in that form.

5. 2-(2-Hydroxyethyl)-cyclododecanol (IV)

The crude ketoester (IX) from step 4 (approximately 180 gm; 0.7 mol) was refluxed for 8 hours with agitation under nitrogen with 74 gm (1.96 mol) of sodium borohydride in 1250 ml of isopropanol. After addition of 150 ml of water, the mixture was agitated for 30 minutes at 60° C., and any sodium borohydride remaining was destroyed by the addition of 100 ml of acetone with good cooling. After agitation for another 30 minutes, the isopropanol was distilled off with the simultaneous addition of 200 ml water. After cooling to approximately 30° to 35° C., the residue was neutralized with half-concentrated sulfuric acid and mixed with 700 ml of toluene. The aqueous phase was separated. The toluene phase contained approximately 135 gm of 1,4-diol (IV) (85% yield) and was used further without evaporation.

6. 13-Oxabicyclo[10.3.0]pentadecane (V)

The toluene solution of the diol from step 5 (approximately 0.59 mol) was mixed with 12 gm of p-toluenesulfonic acid and heated with agitation for approximately 4 hours under a water separator. After the reaction was complete, the mixture was neutralized with 5% sodium hydroxide solution, the aqueous phase was separated, and the toluene phase was evaporated. Approximately 80 gm of 13-oxabicyclo[10.3.0]pentadecane (65% yield) were isolated by vacuum distillation at 90° to 95° C./0.25 mbar.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for preparing 13-oxabicyclo[10.3.0]pentadecane which comprises the steps of:
   (a) reacting cyclododecanone with elemental bromine in an organic solvent to form α-bromocyclododecanone;
   (b) reacting α-bromocyclododecanone with malonic acid dialkyl ester and alkali metal alcoholate to form the ketodiester 2-(2-oxocyclododec-1-yl)-malonic acid dialkyl ester;
   (c) hydrolyzing and decarboxylating the ketodiester from step (b) to form the corresponding 2-oxocyclododec-1-yl-acetic acid in an aqueous alkaline solution;
   (d) purifying the product of step (c) by extraction with an organic solvent and obtaining 2-oxocyclododec-1-yl-acetic acid;
   (e) reacting the product of step (d) with a lower alcohol to form a corresponding ester;
   (f) reducing the product of step (e) with a complex metallic hydride to form 2-(2-hydroxyethyl)-cyclododecanol; and
   (g) heating the product of step (f) in the presence of an acid catalyst to form 13-oxabicyclo[10.3.0]pentadecane.

2. The process of claim 1, wherein step (a) is carried out in boiling methylene chloride as solvent.

3. The process of claim 1, wherein step (b) α-bromocyclododecanone is reacted with sodium malonic acid dimethyl ester in methanol at from about 10° to 40° C.

4. The process of claim 1, wherein step (c) is carried out in a pressure vessel at 200° to 250° C. in the presence of water, followed by further hydrolysis and decarboxylation in an aqueous alkaline solution.

5. The process of claims 1 or 4, wherein crude 2-oxocyclododec-1-yl-acetic acid in the form of the aqueous, alkaline solution of the alkali metal salt is washed with methylisobutyl ketone to remove neutral by-products, optionally after brief additional saponification.

6. The process of claim 1, wherein in step (e) the lower alcohol is methanol.

7. The process of claim 1, wherein in step (f) crude 2-oxocyclododec-1-yl-acetic acid ester is reduced with from about 2.0 to 3.0 mols of sodium borohydride per mol of ketoester in isopropanol as the solvent and under a protective nitrogen atmosphere.

8. The process of claim 1 which comprises the steps of:
   (a) reacting cyclododecanone with elemental bromine in boiling methylene chloride to form α-bromocyclododecanone;
   (b) reacting α-bromocyclododecanone with sodium malonic acid dimethyl ester in methanol at from about 10° to 40° C. to form 2-(2-oxocyclododec-1-yl)-malonic acid dimethyl ester;
   (c) hydrolyzing and decarboxylating the product of step (b) in a pressure vessel at 200° to 250° C. in the presence of water, followed by further hydrolysis and decarboxylation in an aqueous alkaline solution;
   (d) purifying the product of step (c) by extraction with an organic solvent and obtaining 2-oxocyclododec-1-yl-acetic acid;
   (e) reacting the product of step (d) with methanol to form the corresponding ester;
   (f) reducing the product of step (e) with from about 2.0 to 3.0 mols of sodium borohydride per mol of ketoester in propanol as solvent and under a protective nitrogen atmosphere; and
   (g) heating the product of step (f) in the presence of an acid catalyst to form 13-oxabicyclo[10.3.0]pentadecane.

* * * * *